United States Patent
Dai

(10) Patent No.: US 9,546,137 B2
(45) Date of Patent: Jan. 17, 2017

(54) METHODS OF PREPARING TECOVIRIMAT

(71) Applicant: SIGA TECHNOLOGIES INC., Corvallis, OR (US)

(72) Inventor: Dongcheng Dai, Corvallis, OR (US)

(73) Assignee: Siga Technologies Inc., Corvallis, OR (US)

( * ) Notice: Subject to any disclaimer, the term of this patent is extended or adjusted under 35 U.S.C. 154(b) by 0 days.

(21) Appl. No.: 14/420,728

(22) PCT Filed: Aug. 14, 2013

(86) PCT No.: PCT/US2013/054816
§ 371 (c)(1),
(2) Date: Feb. 10, 2015

(87) PCT Pub. No.: WO2014/028545
PCT Pub. Date: Feb. 20, 2014

(65) Prior Publication Data
US 2015/0322010 A1  Nov. 12, 2015

Related U.S. Application Data

(60) Provisional application No. 61/683,905, filed on Aug. 16, 2012.

(51) Int. Cl.
| | | |
|---|---|---|
| *C07D 207/50* | (2006.01) | |
| *C07D 209/56* | (2006.01) | |
| *C07D 209/76* | (2006.01) | |
| *C07D 307/77* | (2006.01) | |

(52) U.S. Cl.
CPC .......... *C07D 209/56* (2013.01); *C07D 207/50* (2013.01); *C07D 209/76* (2013.01); *C07D 307/77* (2013.01)

(58) Field of Classification Search
CPC ... C07D 207/50; C07D 209/56; C07D 209/76; C07D 307/77; A61K 31/4015; A61K 31/403; A61K 31/343

USPC .......... 548/424, 546; 549/457; 514/410, 468
See application file for complete search history.

(56) References Cited

U.S. PATENT DOCUMENTS

| | | |
|---|---|---|
| 7,687,641 B2 | 3/2010 | Jordan et al. |
| 7,737,168 B2 | 6/2010 | Jordan et al. |
| 2007/0003516 A1 | 1/2007 | Almond et al. |
| 2007/0287735 A1 | 12/2007 | Jordan et al. |
| 2008/0004452 A1 | 1/2008 | Jordan et al. |
| 2011/0236434 A1 | 9/2011 | Tyavanagimatt |
| 2012/0020922 A1 | 1/2012 | Jordan et al. |

OTHER PUBLICATIONS

Notification Concerning Transmittal of International Preliminary Report on Patentability (Chapter 1 of the Patent Cooperation Treaty) issued in PCT/US2013/054816, dated Feb. 17, 2015.
Jordan, R. et al., "Development of ST-246® for Treatment of Poxivirus Infections." Viruses. Nov. 3, 2010, vol. 2, pp. 2409-2435.
Yang, G. et al., "An Orally Bioavailable Antipoxvirus Compound (ST-246) Inhibits Extracellular Virus Formation and Protects Mice from Lethal Orthopoxiviorus Challenge." Journal of Virology. Oct. 2005, vol. 79, No. 20, pp. 13139-13149.
Grosenbach, DW et al., "Development of the small-molecule antiviral ST-245® as a smallpox therapeutic." Future Virology. 2011, vol. 6, pp. 653-671.
Bailey, TR et al., "N-(3,3a,4,4a,5,5a,6,6a-Octahydro-1,3-dioxo-4,6-ethenocycloprop[f]isoindol-2-(1H)-yl)carboxamides: Identification of Novel Orthopoxvirus Egress Inhibitors." J. Med. Chem. Mar. 3, 2007.
Chinsangaram, J. et al., Pharmacokinetic Comparison of Single Oral Dose of Polymorph Form I versus form V Capsules of the Antiorhopoxvirus Compound ST-246 in Human Volunteers.: Antimicrobial Agents and Chemotherapy. Apr. 23, 2012, vol. 56, pp. 3582-3586.

*Primary Examiner* — Alicia L Otton
*Assistant Examiner* — Sagar Patel
(74) *Attorney, Agent, or Firm* — Charles C. Achkar; Ostrolenk Faber LLP.

(57) ABSTRACT

Disclosed are methods for the preparation of Tecovirimat for the treatment or prophylaxis of viral infections and diseases associated therewith, particularly those viral infections and associated diseases caused by the orthopoxvirus.

8 Claims, No Drawings

METHODS OF PREPARING TECOVIRIMAT

CROSS REFERENCE TO RELATED APPLICATIONS

This application is a §371 National Phase Application of International Application No. PCT/US2013/054816 filed Aug. 14, 2013, which claims the benefit of U.S. Provisional Patent Application No. 61/683,905, filed on Aug. 16, 2012, the disclosure of which is hereby fully incorporated herein by reference.

FIELD OF THE INVENTION

Described herein are methods for the preparation of Tecovirimat for the treatment or prophylaxis of viral infections and diseases associated therewith, particularly those viral infections and associated diseases caused by the orthopoxvirus. Tecovirimat, with a proprietary name of ST-246®, has a chemical name of N-[(3aR,4R,4aR,5aS,6S,6aS)-3,3a,4,4a,5,5a,6,6a-octahydro-1,3-dioxo-4,6-etheno-cycloprop[f]isoindol-2(1H)-yl]-4-(trifluoromethyl)-benzamide.

BACKGROUND OF THE INVENTION

The Orthopox genus (*Orthopoxviridae*) is a member of the Poxviridae family and the Choropoxivirinae subfamily. The genus consists of numerous viruses that cause significant disease in human and animal populations. Viruses in the orthopox genus include cowpox, monkeypox, vaccinia, and variola (smallpox), all of which can infect humans.

The smallpox (variola) virus is of particular importance. Recent concerns over the use of smallpox virus as a biological weapon have underscored the necessity of developing small molecule therapeutics that target orthopoxviruses. Variola virus is highly transmissible and causes severe disease in humans resulting in high mortality rates (Henderson et al. (1999) JAMA. 281:2127-2137). Moreover, there is precedent for use of variola virus as a biological weapon. During the French and Indian wars (1754-1765), British soldiers distributed blankets used by smallpox patients to American Indians in order to establish epidemics (Stern, E. W. and Stern, A. E. 1945. The effect of smallpox on the destiny of the Amerindian. Boston). The resulting outbreaks caused 50% mortality in some Indian tribes (Stern, E. W. and Stern, A. E.). More recently, the Soviet government launched a program to produce highly virulent weaponized forms of variola in aerosolized suspensions (Henderson, supra). Of more concern is the observation that recombinant forms of poxvirus have been developed that have the potential of causing disease in vaccinated animals (Jackson et al. (2001) J. Virol., 75:1205-1210).

The smallpox vaccine program was terminated in 1972; thus, many individuals are no longer immune to smallpox infection. Even vaccinated individuals may no longer be fully protected, especially against highly virulent or recombinant strains of virus (Downie and McCarthy. (1958) J Hyg. 56:479-487; Jackson, supra). Therefore, mortality rates would be high if variola virus were reintroduced into the human population either deliberately or accidentally.

Variola virus is naturally transmitted via aerosolized droplets to the respiratory mucosa where replication in lymph tissue produces asymptomatic infection that lasts 1-3 days. Virus is disseminated through the lymph to the skin where replication in the small dermal blood vessels and subsequent infection and lysis of adjacent epidermal cells produces skin lesions (Moss, B. (1990) Poxviridae and Their Replication, 2079-2111. In B. N. Fields and D. M. Knipe (eds.), Fields Virology. Raven Press, Ltd., New York). Two forms of disease are associated with variola virus infection; variola major, the most common form of disease, which produces a 30% mortality rate and variola minor, which is less prevalent and rarely leads to death (<1%). Mortality is the result of disseminated intravascular coagulation, hypotension, and cardiovascular collapse, that can be exacerbated by clotting defects in the rare hemorrhagic type of smallpox (Moss, supra).

A recent outbreak of monkeypox virus underscores the need for developing small molecule therapeutics that target viruses in the orthopox genus. Appearance of monkeypox in the US represents an emerging infection. Monkeypox and smallpox cause similar diseases in humans, however mortality for monkeypox is lower (1%).

Vaccination is the current means for preventing orthopox virus disease, particularly smallpox disease. The smallpox vaccine was developed using attenuated strains of vaccinia virus that replicate locally and provide protective immunity against variola virus in greater than 95% of vaccinated individuals (Modlin (2001) MMWR (Morb Mort Wkly Rep) 50:1-25). Adverse advents associated with vaccination occur frequently (1:5000) and include generalized vaccinia and inadvertent transfer of vaccinia from the vaccination site. More serious complications such as encephalitis occur at a rate of 1:300,000, which are often fatal (Modlin, supra). The risk of adverse events is even more pronounced in immunocompromised individuals (Engler et al. (2002) J Allergy Clin Immunol. 110:357-365). Thus, vaccination is contraindicated for people with AIDS or allergic skin diseases (Engler et al.). While protective immunity lasts for many years, the antibody response to smallpox vaccination is significantly reduced 10 to 15 years post inoculation (Downie, supra). In addition, vaccination may not be protective against recombinant forms of orthopoxvirus. A recent study showed that recombinant forms of mousepox virus that express IL-4 cause death in vaccinated mice (Jackson, supra). Given the side effects associated with vaccination, contraindication of immunocompromised individuals, and inability to protect against recombinant strains of virus, better preventatives and/or new therapeutics for treatment of smallpox virus infection are needed.

Vaccinia virus immunoglobulin (VIG) has been used for the treatment of post-vaccination complications. VIG is an isotonic sterile solution of immunoglobulin fraction of plasma derived from individuals who received the vaccinia virus vaccine. It is used to treat eczema vaccinatum and some forms of progressive vaccinia. Since this product is available in limited quantities and difficult to obtain, it has not been indicated for use in the event of a generalized smallpox outbreak (Modlin, supra).

Cidofovir ([(S)-1-(3-hydroxy-2-phosphonylmethoxypropyl)cytosine] [HBMPC]) is a nucleoside analog approved for treatment of CMV retinitis in AIDS patients. Cidofovir has been shown to have activity in vitro against a number of DNA containing viruses including adenovirus, herpesviruses, hepadnaviruses, polyomaviruses, papillomaviruses, and orthopoxviruses (Bronson et al. (1990) Adv. Exp. Med. Biol. 278:277-83; De Clercq et al. (1987) Antiviral Res. 8:261-272; de Oliveira et al. (1996) Antiviral Res. 31:165-172; Snoeck et al. (2001) Clin Infect. Dis. 33:597-602). Cidofovir has also been found to inhibit authentic variola virus replication (Smee et al. (2002) Antimicrob. Agents Chemother. 46:1329-1335).

However, cidofovir administration is associated with a number of issues. Cidofovir is poorly bioavailable and must be administered intravenously (Laezari et al. (1997) Ann. Intern. Med. 126:257-263). Moreover, cidofovir produces dose-limiting nephrotoxicity upon intravenous administration (Lalezari et al.). In addition, cidofovir-resistance has been noted for multiple viruses. Cidofovir-resistant cowpox, monkeypox, vaccinia, and camelpox virus variants have been isolated in the laboratory by repeated passage in the presence of drug (Smee, supra). Cidofovir-resistance represents a significant limitation for use of this compound to treat orthopoxvirus replication. Thus, the poor bioavailability, need for intravenous administration, and prevalence of resistant virus underscores the need for development of additional and alternative therapies to treat orthopoxvirus infection.

In addition to viral polymerase inhibitors such as cidofovir, a number of other compounds have been reported to inhibit orthopoxvirus replication (De Clercq. (2001) Clin Microbiol. Rev. 14:382-397). Historically, methisazone, the prototypical thiosemicarbazone, has been used in the prophylactic treatment of smallpox infections (Bauer et al. (1969) Am. J Epidemiol. 90:130-145). However, this compound class has not garnered much attention since the eradication of smallpox due to generally unacceptable side effects such as severe nausea and vomiting. Mechanism of action studies suggest that methisazone interferes with translation of L genes (De Clercq (2001), supra). Like cidofovir, methisazone is a relatively non-specific antiviral compound and can inhibit a number of other viruses including adenoviruses, picornaviruses, reoviruses, arboviruses, and myxoviruses (Id.).

Another class of compounds potentially useful for the treatment of poxviruses is represented by inhibitors of S-adenosylhomocysteine hydrolase (SAH). This enzyme is responsible for the conversion of S-adenosylhomocysteine to adenosine and homocysteine, a necessary step in the methylation and maturation of viral mRNA. Inhibitors of this enzyme have shown efficacy at inhibiting vaccinia virus in vitro and in vivo (De Clercq et al. (1998) Nucleosides Nucleotides. 17:625-634.). Structurally, all active inhibitors reported to date are analogues of the nucleoside adenosine. Many are carbocyclic derivatives, exemplified by Neplanacin A and 3-Deazaneplanacin A. While these compounds have shown some efficacy in animal models, like many nucleoside analogues, they suffer from general toxicity and/or poor pharmacokinetic properties (Coulombe et al. (1995) Eur. J Drug Metab Pharmacokinet. 20:197-202; Obara et al. (1996) J Med. Chem. 39:3847-3852). It is unlikely that these compounds can be administered orally, and it is currently unclear whether they can act prophylactically against smallpox infections. Identification of non-nucleoside inhibitors of SAH hydrolase, and other chemically tractable variola virus genome targets that are orally bioavailable and possess desirable pharmacokinetic (PK) and absorption, distribution, metabolism, excretion (ADME) properties would be a significant improvement over the reported nucleoside analogues. In summary, currently available compounds that inhibit smallpox virus replication are generally non-specific and suffer from use limiting toxicities and/or questionable efficacies.

In U.S. Pat. No. 6,433,016 (Aug. 13, 2002) and U.S. Application Publication 2002/0193443 A1 (published Dec. 19, 2002) a series of imidodisulfamide derivatives are described as being useful for orthopoxvirus infections.

New therapies and preventatives are clearly needed for infections and diseases caused by orthopoxvirus infection.

The co-owned PCT application WO 2004/112718 (published Dec. 29, 2004) discloses the use of di, tri, and tetracyclic acylhydrazide derivatives and analogs, as well as pharmaceutical compositions containing the same, for the treatment or prophylaxis of viral infections and diseases associated therewith, particularly those viral infections and associated diseases caused by the orthopoxvirus. The co-owned U.S. Patent application 2008/0004452 (published Jan. 3, 2008) further discloses a process for producing ST-246. However, the current process encounters diastereoselectivity (endo vs. exo), low yields for some steps, use of a genotoxic compound and a very hydroscopic anhydride, and difficulties in securing some raw materials. Thus, there remains an urgent need to develop more effective processes for producing ST-246

SUMMARY OF THE INVENTION

The present invention provides a process for making ST-246 outlined in Scheme 1

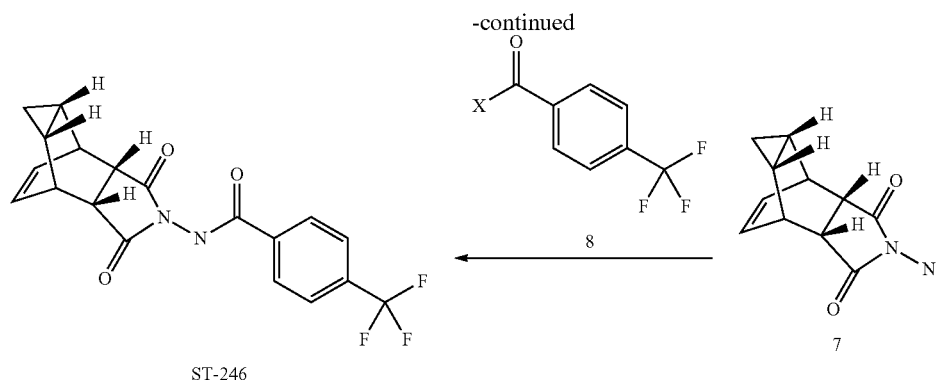
ST-246
P = Boc
The present invention also provides a process for making ST-246 outlined in Scheme 2
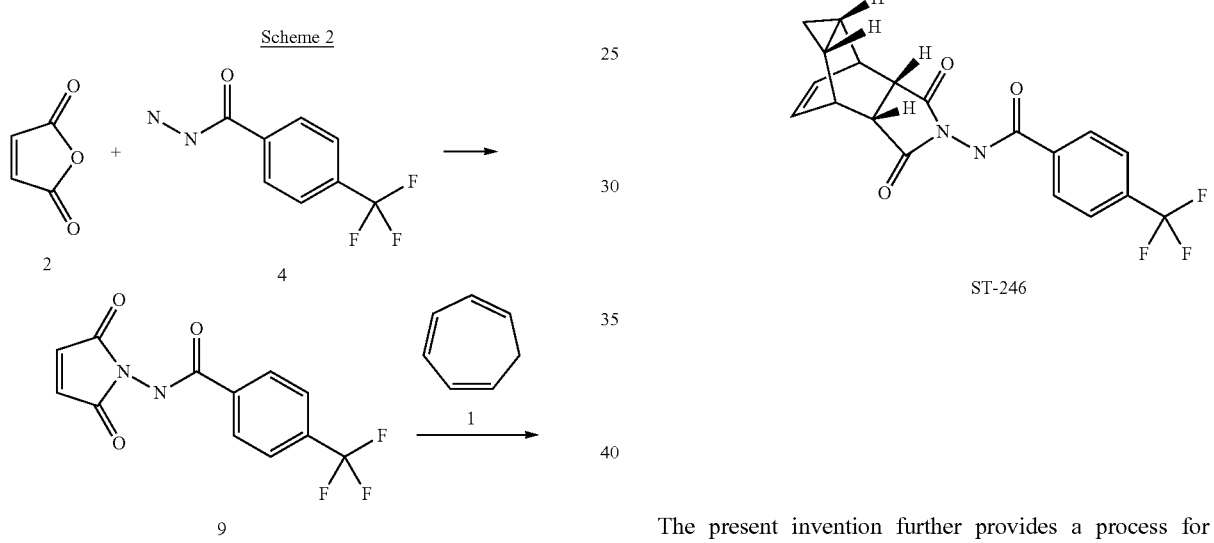
The present invention further provides a process for making ST-246 outlined in Scheme 3
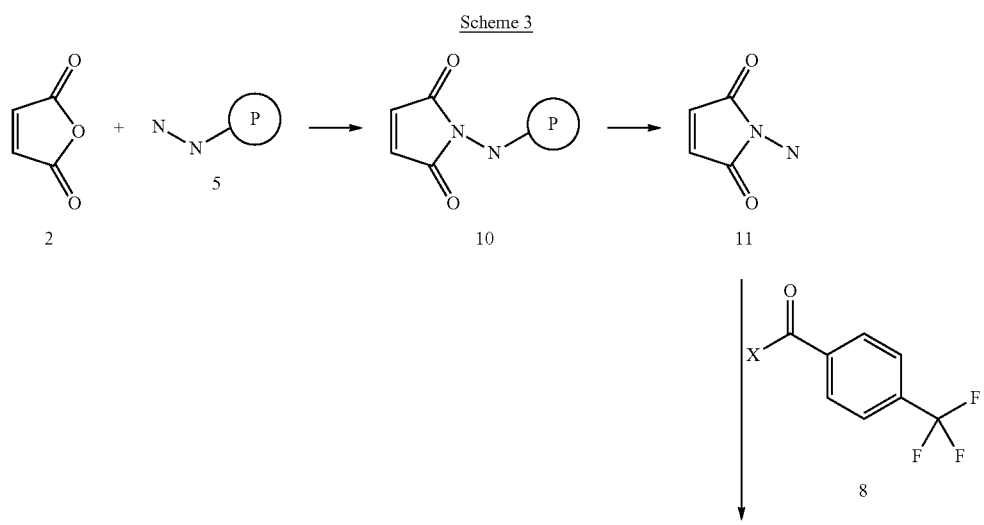

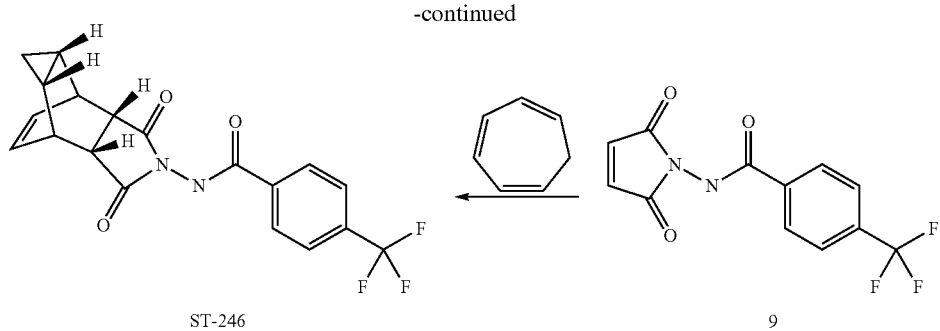
ST-246
P = Boc
The present invention also provides a process for making ST-246 outlined in Scheme 4
Scheme 4
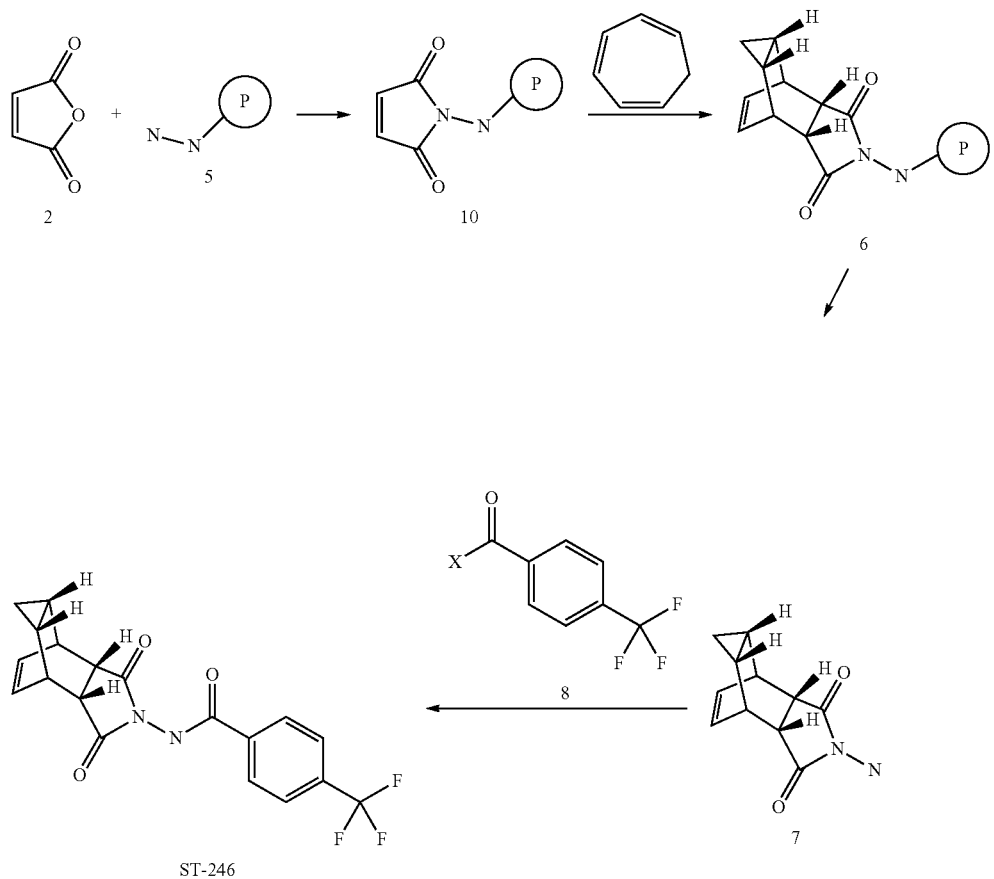
ST-246
P = Boc The present invention further provides a process for making ST-246 outlined in Scheme 5

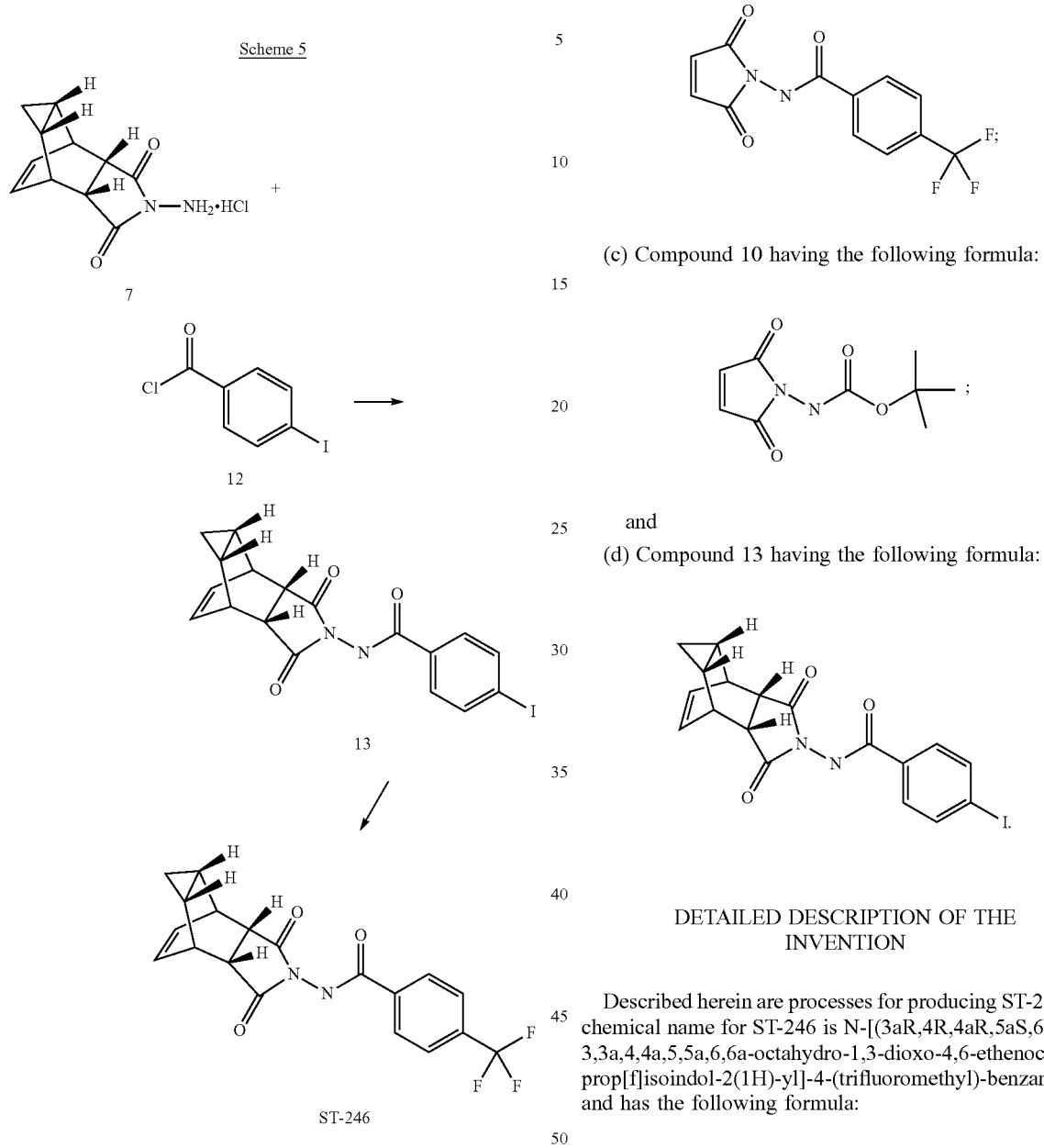

The present invention also provides the following compounds useful in the synthesis of ST-246:

(a) Compound 6 having the following formula:

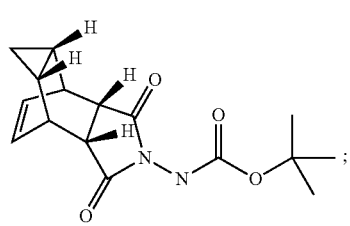

(b) Compound 9 having the following formula:

(c) Compound 10 having the following formula:

and
(d) Compound 13 having the following formula:

DETAILED DESCRIPTION OF THE INVENTION

Described herein are processes for producing ST-246. The chemical name for ST-246 is N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide and has the following formula:

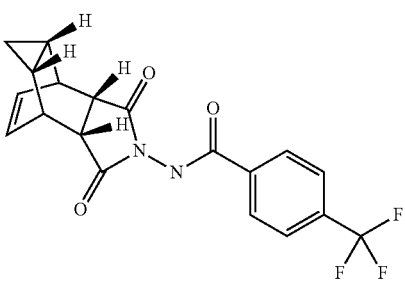

ST-246

Accordingly, it has been discovered that ST-246 can be prepared by a process called Synthetic Route I, said process comprising:

(a) reacting compound 3 of formula:

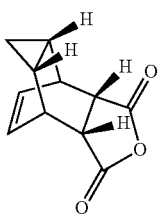

with tert-butyl carbazate (compound 5) to form compound 6 of formula:

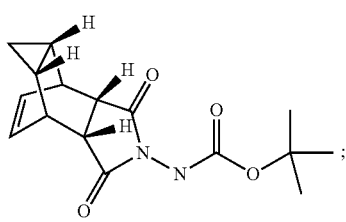

(b) reacting compound 6 with an acid to form compound 7 or salt thereof of formula:

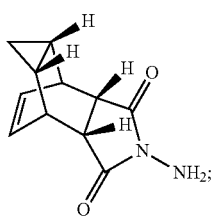

(c) reacting compound 7 with 4-(trifluoromethyl)benzoyl chloride (compound 8); and
(d) collecting N-[(3aR,4R,4aR,5aS,6S,6aS)-3,3a,4,4a,5, 5a,6,6a-octahydro-1,3-dioxo-4,6-ethenocycloprop[f] isoindol-2(1H)-yl]-4-(trifluoromethyl)-benzamide.

For Synthetic Route I, the acid in step (b) is preferably HCl. Also preferably, compound 6 is dissolved in in i-PrOAc prior to the reaction of step (b). Again preferably, a base is present in the reaction of step (c), wherein said base is selected from the group consisting of: pyridine, 4-dimethylaminopyridine, triethylamine and diisopropylethylamine. Step (c) is preferably carried out at a temperature of less than about 20° C.

It has been also discovered that ST-246 can be prepared by a process called Synthetic Route II, said process comprising:
(a) reacting compound 4 of formula:

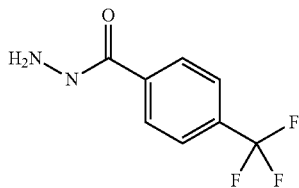 [SMILES: NNC(=O)c1ccc(C(F)(F)F)cc1]

with maleic anhydride (compound 2) to form compound 9 of formula:

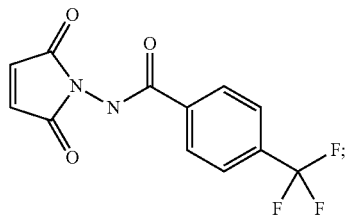 [SMILES: O=C(NN1C(=O)C=CC1=O)c1ccc(C(F)(F)F)cc1]

(b) reacting compound 9 with cycloheptatriene (compound 1); and
(c) collecting N-[(3aR,4R,4aR,5aS,6S,6aS)-3,3a,4,4a,5, 5a,6,6a-octahydro-1,3-dioxo-4,6-ethenocycloprop[f] isoindol-2(1H)-yl]-4-(trifluoromethyl)-benzamide.

For Synthetic Route II, step (a) is preferably carried out in o-xylene and reactants heated to reflux. Also preferably, step (b) is carried out in toluene at a temperature of at least about 75° C.

It has been further discovered that ST-246 can be prepared by a process called Synthetic Route III, said process comprising:
(a) reacting maleic anhydride (compound 2) and tert-butyl carbazate (compound 5) to form compound 10 of formula:

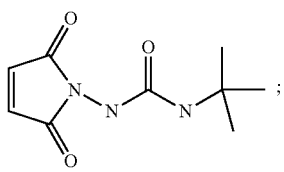

(b) reacting compound 10 with an acid to form compound 11 or salt thereof of formula:

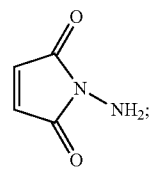

(c) reacting compound 11 with 4-(trifluoromethyl)benzoyl halide (compound 8) to form compound 9 of formula:

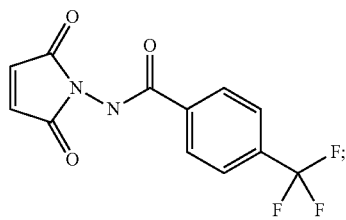 [SMILES: O=C(NN1C(=O)C=CC1=O)c1ccc(C(F)(F)F)cc1]

(d) reacting compound 9 with cycloheptatriene (compound 1); and
(e) collecting N-[(3aR,4R,4aR,5aS,6S,6aS)-3,3a,4,4a,5, 5a,6,6a-octahydro-1,3-dioxo-4,6-ethenocycloprop[f] isoindol-2(1H)-yl]-4-(trifluoromethyl)-benzamide.

For Synthetic Route III, step (a) is preferably carried out in anhydrous toluene under nitrogen atmosphere and reactants heated to reflux. Also preferably, the acid in step (b) is HCl. It is also preferred that compound 10 is dissolved in i-PrOAc prior to the reaction of step (b). Furthermore, a base is preferably present in the reaction of step (c), wherein said base is selected from the group consisting of: pyridine, 4-dimethylaminopyridine, triethylamine and diisopropylethylamine. Also preferably, the 4-(trifluoromethyl)benzoyl halide is 4-(trifluoromethyl)benzoyl chloride. Step (c) is preferably carried out at a temperature of about 10 to about 25° C. and step (d) is carried out in toluene under nitrogen atmosphere at a temperature above about 110° C.

It has been further discovered that ST-246 can be prepared by a process called Synthetic Route IV, said process comprising:

(a) reacting maleic anhydride (compound 2) and tert-butyl carbazate (compound 5) to form compound 10 of formula:

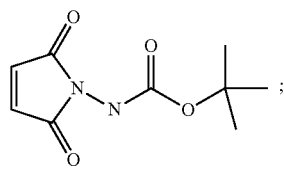

(b) reacting compound 10 with cycloheptatriene (compound 1) to form compound 6 with the formula:

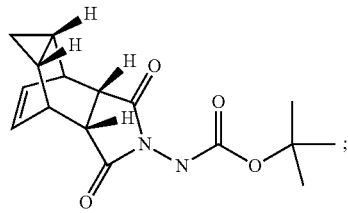

(c) reacting compound 6 with an acid to form compound 7 or salt thereof of formula:

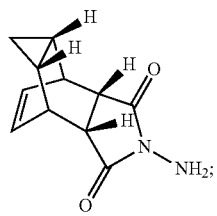

(d) reacting compound 7 with 4-(trifluoromethyl)benzoyl chloride (compound 8); and (e) collecting N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide.

For Synthetic Route IV, step (a) is preferably carried out in anhydrous toluene under nitrogen atmosphere and reactants heated to reflux. Also preferably, step (b) is carried out under nitrogen atmosphere at a temperature of at least about 75° C. The acid in step (c) is preferably HCl. It is also preferred that compound 6 is dissolved in in i-PrOAc prior to the reaction of step (c). Also preferably, a base is present in the reaction of step (d), wherein said base is selected from the group consisting of: pyridine, 4-dimethylaminopyridine, triethylamine and diisopropylethylamine. Step (d) is carried out at a preferred temperature of less than about 20° C.

It has been further discovered that ST-246 can be prepared by a process called Synthetic Route V, said process comprising:

(a) reacting compound 7 having formula:

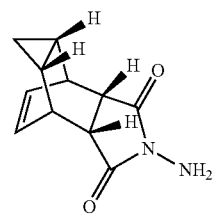

with 4-Iodobenzoyl chloride (compound 12) to form compound 13 having formula:

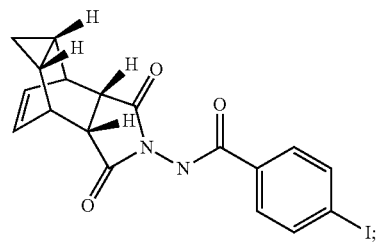

(b) reacting compound 13 with methyl 2,2-difluoro-2-(fluorosulfonyl)acetate; and (c) collecting N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide.

For synthetic Route V, a base is preferably present in the reaction of step (a), wherein said base is selected from the group consisting of: pyridine, 4-dimethylaminopyridine, triethylamine and diisopropylethylamine. Also preferably, step (a) is carried out under nitrogen atmosphere at a temperature below about 20° C. and step (b) is carried out in the presence of dimethylformamide, methyl 2,2-difluoro-2-(fluorosulfonyl)acetate and copper (I) iodide.

Optionally, the ST-246 collected in each of the Synthetic Routes I-V step is further purified by column chromatography.

EXAMPLE 1

Synthetic Route I

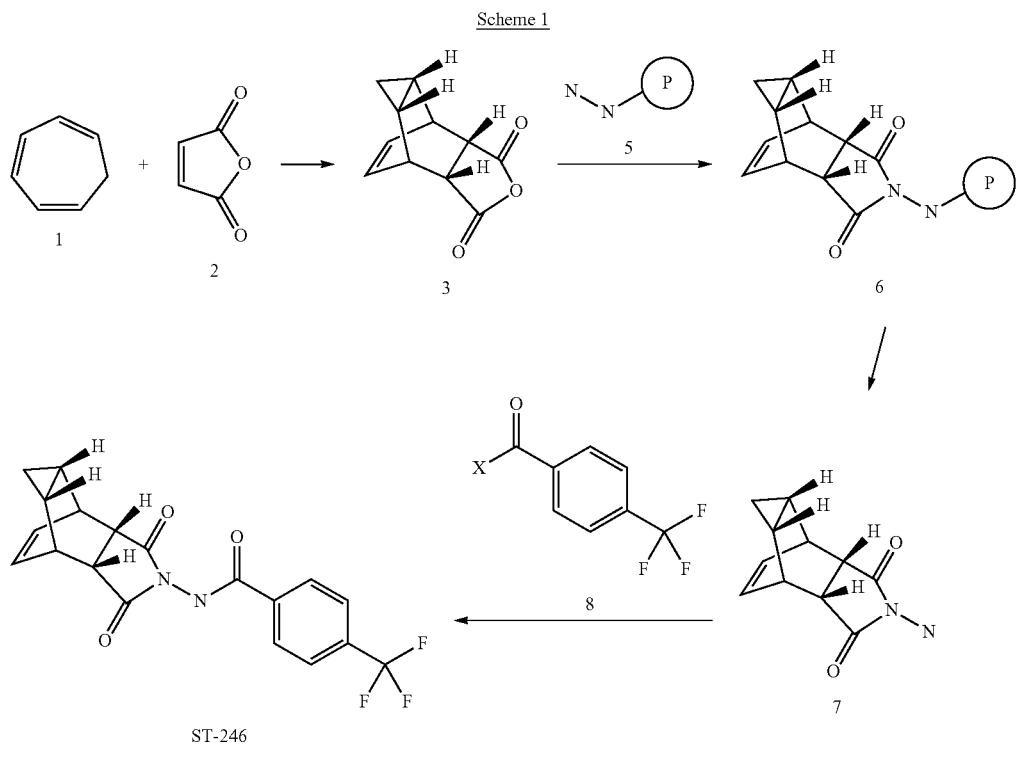

P = Boc

Step A. Synthesis of Compound 6 (P=Boc)

To a mixture of compound 3 (5.0 g, 26.3 mmol, synthesized according to WO04112718) in EtOH (80 mL, EMD, AX0441-3) was added tert-butyl carbazate 5 (3.65 g, 27.6 mmol, Aldrich, 98%). The reaction mixture was heated to reflux for 4 h under nitrogen atmosphere. LC-MS analysis of the reaction mixture showed less than 5% of compound 3 remained. The reaction mixture was evaporated under reduced pressure. The residue was recrystallized from EtOAc-hexanes, the solid was filtered, washed with hexanes (50 mL) and dried under vacuum to afford compound 6 (3.1 g, 39% yield) as a white solid. The filtrate was concentrated and purified by column chromatography eluting with 25% EtOAc in hexanes to give an additional 3.64 g (46% yield) of compound 6 as a white solid. Total yield: 6.74 g (84% yield). $^1$H NMR in CDCl$_3$: δ 6.30 (br s, 1H), 5.79 (t, 2H), 3.43 (s, 2H), 3.04 (s, 2H), 1.46 (s, 9H), 1.06-1.16 (m, 2H), 0.18-0.36 (m, 2H); Mass Spec: 327.2 (M+Na)$^+$

Step B. Synthesis of Compound 7 (HCl Salt)

Compound 6 (3.6 g, 11.83 mmol) was dissolved in i-PrOAc (65 mL, Aldrich, 99.6%). 4M HCl in dioxane (10.4 mL, 41.4 mmol, Aldrich) was added drop-wise to the above solution keeping the temperature below 20° C. The reaction mixture was stirred at room temperature overnight (18 h) under nitrogen atmosphere. The resulting solid was filtered, washed with i-PrOAc (15 mL) and dried under vacuum to yield HCl salt of compound 7 (1.9 g, 67% yield) as a white solid. The filtrate was concentrated to ⅓ its volume and stirred at 10-15° C. for 30 min. The solid was filtered, washed with minimal volume of i-PrOAc and dried to afford additional 0.6 g (21% yield) of compound 7. Total yield: 2.5 g (88% yield). $^1$H NMR in DMSO-d6: δ 6.72 (br s, 3H), 5.68 (m, 2H), 3.20 (s, 2H), 3.01 (s, 2H), 1.07-1.17 (m, 2H), 0.18-0.29 (m, 1H), −0.01-0.07 (m, 1H); Mass Spec: 205.1 (M+H)$^+$

Step C. Synthesis of ST-246

To a mixture of compound 7 (0.96 g, 4 mmol) in dry dichloromethane (19 mL) was added triethylamine (1.17 mL, 8.4 mmol, Aldrich) keeping the temperature below 20° C. The resulting solution was stirred for 5 minutes at 15-20° C., to it was added drop-wise 4-(trifluoromethyl)benzoyl chloride 8 (0.63 mL, 4.2 mmol, Aldrich, 97%) and the reaction mixture was stirred at room temperature overnight (18 h). LC-MS and TLC analysis showed the correct molecular weight and R$_f$ value of ST-246 but the reaction was not complete. Additional 0.3 mL (2 mmol, 0.5 eq) of 4-(trifluoromethyl)benzoyl chloride 8 was added to the reaction mixture at 15-20° C. The reaction was then stirred at room temperature overnight (19 h). LC-MS analysis indicated ca. 5% of starting material 7 still remained. The reaction was stopped and dichloromethane (30 mL) was added. The organic phase was washed with water (30 mL), saturated aqueous NH$_4$Cl (30 mL), water (15 mL) and saturated aqueous NaHCO$_3$ (30 mL). The organic phase was separated, dried over Na$_2$SO$_4$, filtered and concentrated to give crude product. The crude product was purified by column chromatography eluting with 30-50% EtOAc in hexanes to afford ST-246 (0.34 g, 23% yield) as an off-white solid. Analytical data ($^1$H NMR, LC-MS and HPLC by co-injection) were matched with those of ST-246 synthesized according to WO04112718 and were consistent.

EXAMPLE 2

Synthetic Route II

Scheme 2

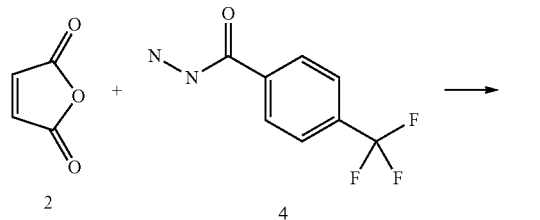

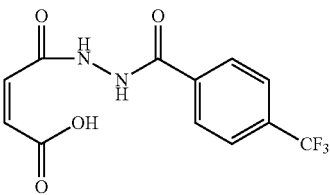

Uncyclized product (MS = 303)

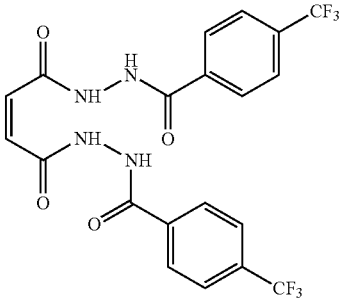

Dimer by-product (MS = 489)

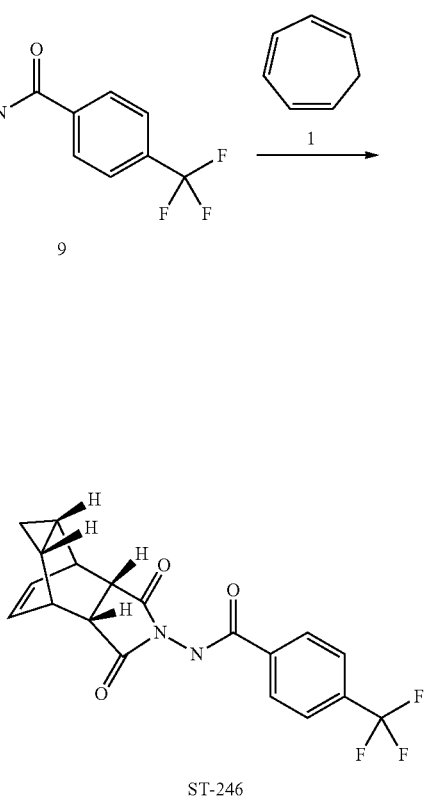

Step A. Synthesis of Compound 9

A mixture of compound 4 (2.0 g, 9.8 mmol) and maleic anhydride 2 (0.96 g, 9.8 mmol, Aldrich powder, 95%) in o-xylene (100 mL, Aldrich anhydrous, 97%) was heated to reflux using a Dean-Stark trap apparatus overnight. After 18 h, LC-MS analysis at 215 nm showed the desired product 9 (86%), an uncyclized product (2.6%) and a dimer by-product (11.6%). The reaction mixture was cooled to 45° C. and evaporated under reduced pressure. The residue was dissolved in EtOAc (50 mL) and the insoluble solid (mostly uncyclized product) was removed by filtration. The filtrate was concentrated and purified by column chromatography eluting with 50% EtOAc in hexanes to yield compound 9 (1.5 g, 54% yield) as an off-white solid. $^1$H NMR in CDCl$_3$: δ 8.44 (s, 1H), 7.91 (d, 2H), 7.68 (d, 2H), 6.88 (s, 2H); Mass Spec: 285.1 (M+H)$^+$

Step B. Synthesis of ST-246 (Route II)

A mixture of compound 9 (0.97 g, 3.4 mmol) and cycloheptatriene 1 (0.51 mL, 4.42 mmol, distilled before use, Aldrich tech 90%) in toluene (50 mL, Aldrich anhydrous) was heated at 95° C. under nitrogen atmosphere. After 1.5 h at 95° C., LC-MS analysis at 254 nm showed 29% conversion to the desired product (endo:exo=94:6). The resulting solution was continued to be heated at same temperature overnight. After 18 h at 95° C., LC-MS analysis indicated 75% conversion with an endo:exo ratio of 94:6. The reaction temperature was increased to 110° C. and the reaction was monitored. After heating at 110° C. for 7 h, LC-MS analysis at 254 nm showed 96.4% conversion to the desired product (endo:exo=94:6). The volatiles were removed by evaporation under reduced pressure and the reside was purified by column chromatography eluting with 30% EtOAc in hexanes to afford ST-246 (0.29 g, 22.6% yield, HPLC area 99.7% pure and 100% endo isomer) as a white solid. Analytical data ($^1$H NMR, LC-MS and HPLC by co-injection) were matched with those of ST-246 synthesized according to WO04112718 and were consistent. An additional 0.5 g of ST-246 (38.9% yield, endo:exo=97:3) was recovered from column chromatography. Total Yield: 0.84 g (65.4% yield). $^1$H NMR of ST-246 exo isomer in CDCl$_3$: δ 8.62 (s, 1H), 7.92 (d, 2H), 7.68 (d, 2H), 5.96 (m, 2H), 3.43 (s, 2H), 2.88 (s, 2H), 1.17 (s, 2H), 0.24 (q, 1H), 0.13 (m, 1H); Mass Spec: 377.1 (M+H)$^+$

EXAMPLE 3

Synthetic Route III

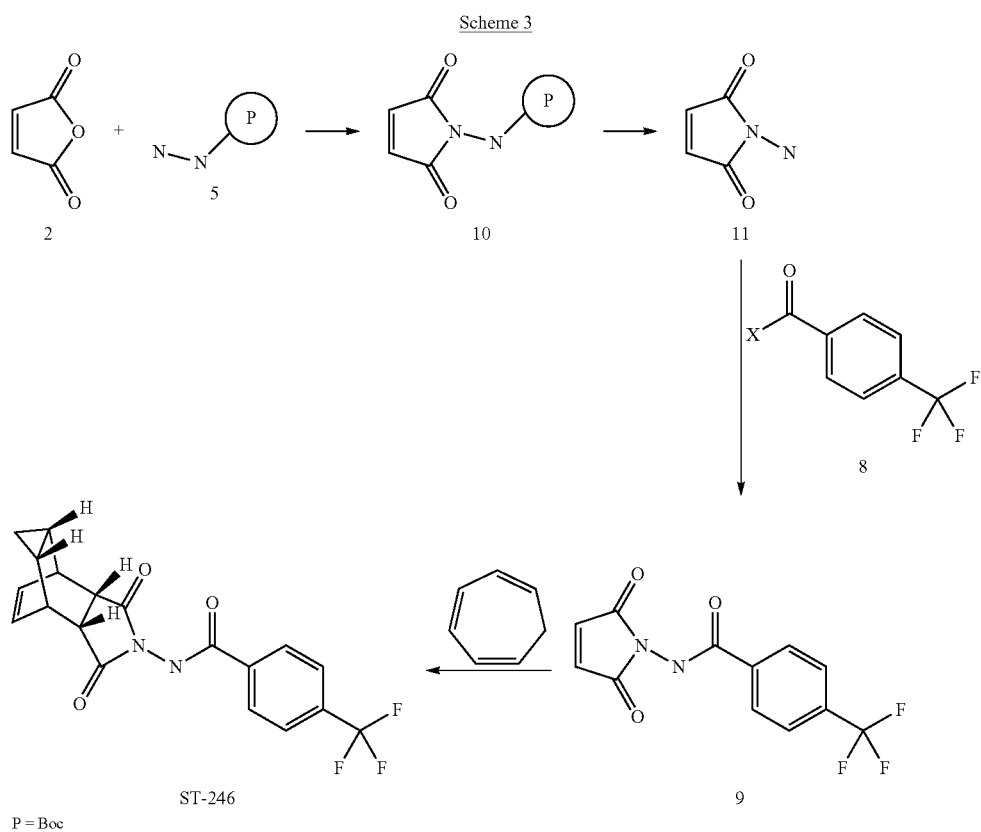

Scheme 3

ST-246

P = Boc

Step A. Synthesis of Compound 10

A mixture of maleic anhydride 2 (15.2 g, 155 mmol, Aldrich powder 95%) and tert-butyl carbazate 5 (20.5 g, 155 mmol, Aldrich, 98%) in anhydrous toluene (150 mL, Aldrich anhydrous) was heated to reflux using a Dean-Stark trap apparatus under nitrogen atmosphere. After refluxing for 2 h, no starting material 2 remained and LC-MS analysis at 254 nm showed the desired product 10 (20% by HPLC area), imine by-product (18%) and disubstituted by-product (56%). The reaction mixture was concentrated and purified by column chromatography eluting with 25% EtOAc in hexanes to afford compound 10 (5.98 g, 18% yield, HPLC area >99.5% pure) as a white solid. $^1$H NMR in DMSO-d6: δ 9.61 (s, 1H), 7.16 (s, 2H), 1.42 (s, 9H); Mass Spec: 235.1 (M+Na)$^+$.

Imine by-product

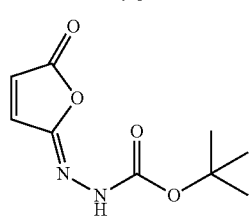

C$_9$H$_{12}$N$_2$O$_4$
Mol. Wt.: 212.2

-continued
Disubstituted by-product

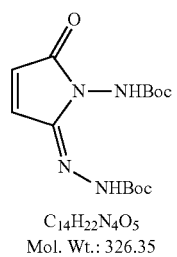

C$_{14}$H$_{22}$N$_4$O$_5$
Mol. Wt.: 326.35

Step B. Synthesis of Compound 11 (HCl salt)

Compound 10 (3.82 g, 18 mmol) was dissolved in i-PrOAc (57 mL, Aldrich, 99.6%). 4M HCl in dioxane (15.8 mL, 63 mmol, Aldrich) was added drop-wise to the above solution keeping the temperature below 20° C. The solution was stirred overnight (24 h) at room temperature under nitrogen atmosphere. The resulting solid was filtered, washed with i-PrOAc (10 mL) and dried at 45° C. under vacuum for 1 h to afford HCl salt of compound 11 (2.39 g, 89% yield) as a white solid. $^1$H NMR in CD$_3$OD: δ 6.98 (s, 2H); Mass Spec: 113.0 (M+H)$^+$

Step C. Synthesis of Compound 9 (Route III)

To a mixture of compound 11 (1.19 g, 8 mmol) in dry dichloromethane (24 mL) was added diisopropylethylamine (2.93 mL, 16.8 mmol, Aldrich redistilled grade) keeping the temperature below 20° C. The resulting solution was stirred for 5 minute at 15-20° C. and to it was added 4-(trifluoromethyl)benzoyl chloride 8 (1.31 mL, 8.8 mmol, Aldrich, 97%) drop-wise. The reaction was stirred at room temperature for 5 h. LC-MS analysis showed the correct MW but the reaction was not complete. Additional 0.48 mL (0.4 equiv) of 4-(trifluoromethyl)benzoyl chloride 8 was added to the reaction mixture at 15-20° C. and the reaction mixture was stirred at room temperature overnight (21 h). The reaction was stopped and dichloromethane (50 mL) was added. The organic phase was washed with water (50 mL), saturated aqueous $NH_4Cl$ (50 mL), water (30 mL) and saturated aqueous $NaHCO_3$ (30 mL). The organic phase was separated, dried over $Na_2SO_4$, filtered and concentrated to give crude product. The crude product was purified by column chromatography eluting with 30-35% EtOAc in hexanes to afford compound 9 (0.8 g, 35% yield) as a light pink solid. Analytical data ($^1$H NMR and LC-MS) were consistent with those of compound 9 obtained in Synthetic Route II.

Step D. Synthesis of ST-246 (Route III)

A mixture of compound 9 (0.5 g, 1.76 mmol) and cycloheptatriene 1 (0.33 mL, 3.17 mmol, distilled before to use, Aldrich tech 90%) in toluene (10 mL, Aldrich anhydrous) was heated at 110-115° C. under nitrogen atmosphere. After 6 h, LC-MS analysis at 254 nm showed 95% conversion to the desired product (endo:exo=94:6). The resulting solution was heated at same temperature overnight (22 h). LC-MS analysis at 254 nm showed no starting material 9 remained and the desired product (endo:exo=93:7). The reaction mixture was concentrated and purified by column chromatography eluting with 25-35% EtOAc in hexanes to afford ST-246 (0.39 g, HPLC area >99.5% pure with a ratio of endo:exo=99:1) as a white solid. Analytical data ($^1$H NMR, LC-MS and HPLC by co-injection) were compared with those of ST-246 synthesized according to WO04112718 and were found to be consistent. An additional 0.18 g of ST-246 (HPLC area >99.5% pure, endo:exo=91:9) was recovered from column chromatography. Total Yield: 0.57 g (86% yield).

EXAMPLE 4

Synthetic Route IV

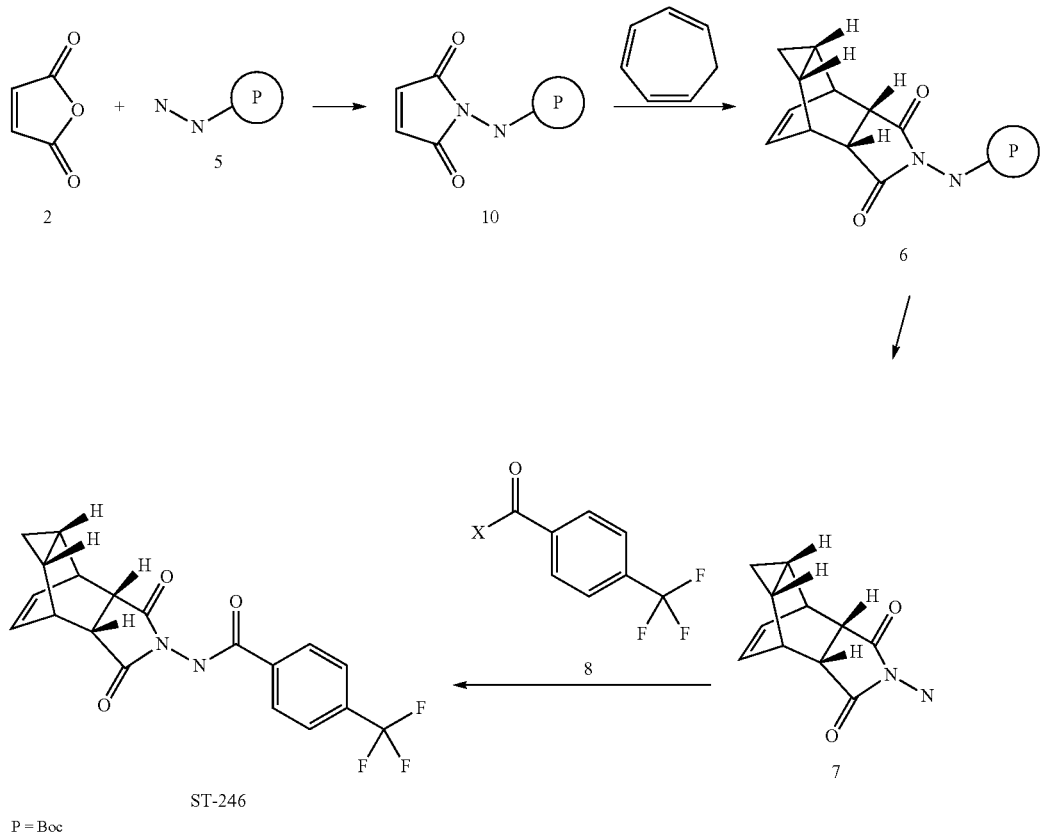

Scheme 4

P = Boc

Step A. Synthesis of Compound 10

A mixture of maleic anhydride 2 (3.4 g, 34.67 mmol, Aldrich powder, 95%) and tert-butyl carbazate 5 (4.6 g, 34.67 mmol, Aldrich, 98%) in anhydrous toluene (51 mL, Aldrich) was heated to reflux using a Dean-Stark trap apparatus under nitrogen atmosphere. After refluxing for 2.5 h, no starting material 2 remained and LC-MS analysis at 254 nm showed the desired product 10 (19% HPLC area), imine by-product (18%) and another by-product (56%). The reaction mixture was concentrated and purified by column chromatography eluting with 30% EtOAc in hexanes to afford compound 10 (1.0 g, 13.6% yield, HPLC area >99% pure) as a white solid. Analytical data ($^1$H NMR and LC-MS) were consistent with those of compound 10 obtained in Synthetic Route III.

Imine by-product

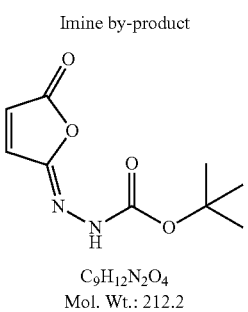

C₉H₁₂N₂O₄
Mol. Wt.: 212.2

Step B. Synthesis of Compound 6

A mixture of compound 10 (4.4 g, 20.74 mmol) and cycloheptatriene 1 (3.22 mL, 31.1 mmol, distilled before to use, Aldrich tech 90%) in toluene (88 mL, 20 volume, Aldrich anhydrous) was heated at 95° C. under nitrogen atmosphere. After 15 h at 95° C., LC-MS analysis showed 83% conversion to the desired product. The reaction mixture was heated at 105° C. overnight. After total 40 h at 95-105° C., LC-MS analysis at 254 nm showed ~99% conversion to the desired product (endo:exo=93:7). The reaction mixture was concentrated and the crude was purified by column chromatography eluting with 25-50% EtOAc in hexanes to afford compound 6 (2.06 g, 32.6% yield, HPLC area 99.9% pure and 100% endo isomer) as a white solid. ¹H NMR and LC-MS were consistent with those of compound 6 obtained in Synthetic Route I. An additional 4.0 g of 6 (63.4% yield, HPLC area 93% pure with a ratio of endo:exo=91:9) was recovered from column chromatography. Total Yield: 6.06 g (96% yield).

Step C. Synthesis of Compound 7 (HCl salt)

Compound 6 (2.05 g, 6.74 mmol) was dissolved in i-PrOAc (26 mL, Aldrich, 99.6%). 4M HCl in dioxane (5.9 mL, 23.58 mmol, Aldrich) was added drop-wise to the above solution keeping the temperature below 20° C. The solution was stirred overnight (18 h) at room temperature under nitrogen atmosphere. The resulting solid was filtered, washed with i-PrOAc (5 mL) and dried under vacuum to yield HCl salt of compound 7 (1.57 g, 97% yield) as a white solid. Analytical data (¹H NMR and LC-MS) were consistent with those of compound 7 in Synthetic Route I.

Step D. Synthesis of ST-246 (Route IV)

To a mixture of compound 7 (0.84 g, 3.5 mmol) in dichloromethane (13 mL) was added diisopropylethylamine (1.34 mL, 7.7 mmol) keeping the temperature below 20° C. and the resulting solution was stirred for 5-10 minutes. 4-(Trifluoromethyl)benzoyl chloride 8 (0.57 mL, 3.85 mmol, Aldrich, 97%) was added to above solution keeping the temperature below 20° C. The reaction mixture was stirred at room temperature for 2 h. Additional 0.2 mL (0.4 equiv) of 4-(trifluoromethyl)benzoyl chloride 8 was added to the reaction keeping the temperature below 20° C. The reaction was stirred at room temperature overnight (24 h). The reaction mixture was diluted with dichloromethane (20 mL). The organic phase was washed with water (20 mL), saturated aqueous NH₄Cl (20 mL), water (20 mL) and saturated aqueous NaHCO₃ (20 mL). The organic phase was separated, dried over Na₂SO₄, filtered and concentrated to give crude product. The crude product was purified by column chromatography eluting with 30-35% EtOAc in hexanes to afford ST-246 (0.25 g, 19% yield, HPLC area >99.5% pure) as a white solid. Analytical data (¹H NMR and LC-MS) were consistent with those of ST-246 synthesized according to WO04112718.

EXAMPLE 5

Synthetic Route V

Scheme 5

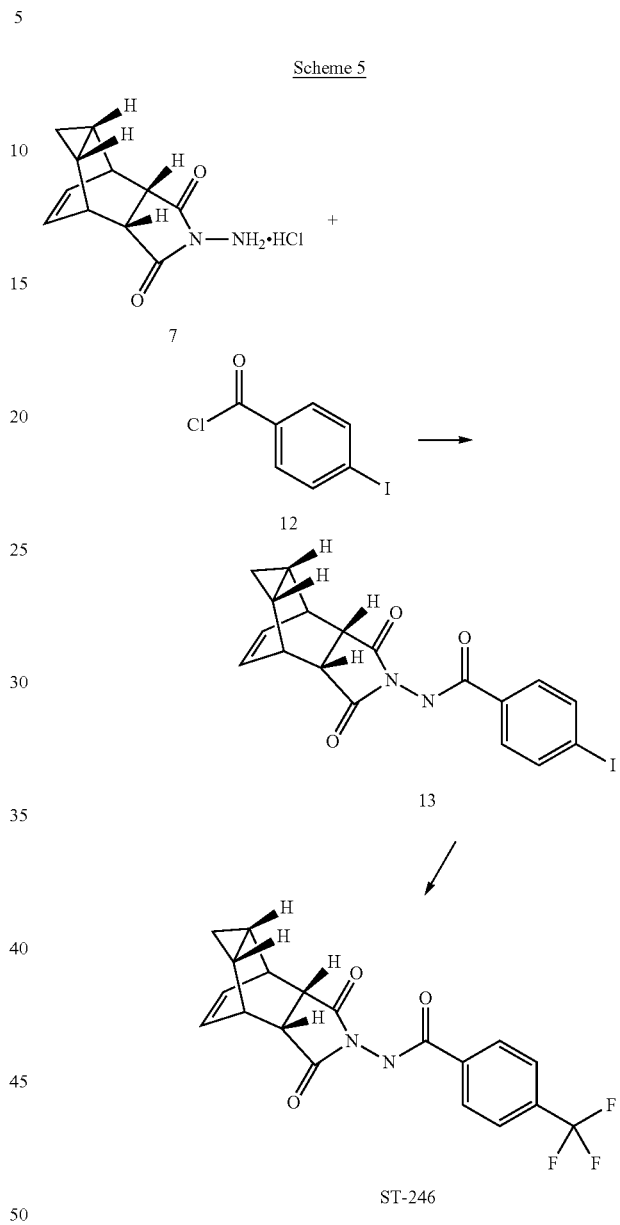

Step A. Synthesis of Compound 13

To a mixture of compound 7 (1.6 g, 6.65 mmol, synthesized according to Synthetic Route I) in dichloromethane (80 mL,) was added triethylamine (2.04 mL, 14.63 mmol) keeping the temperature below 20° C. and the resulting solution was stirred for 5-10 minute. 4-Iodobenzoyl chloride 12 (1.95 g, 7.31 mmol, 1.1 equiv, Aldrich) was added portion-wise under nitrogen atmosphere to the above solution keeping the temperature below 20° C. The reaction mixture was stirred at room temperature overnight. After 17 h and 19 h, additional 0.35 g (0.2 equiv) of acid chloride 12 was added to the reaction keeping the temperature below 20° C. After 24 h, additional 0.18 g (0.1 equiv, used total 1.6 equiv) of acid chloride 12 was added and the reaction was continued to stir at room temperature overnight (total 43 h). LC-MS analysis at 215 nm showed 43% of the desired product (13) and ~5% of compound 7. The reaction was diluted with dichloromethane (100 mL). The organic phase was washed with saturated aqueous NH₄Cl (100 mL), water (100 mL) and saturated aqueous NaHCO₃ (100 mL). The organic phase was separated, dried over Na₂SO₄, filtered and concentrated to give crude product. The crude product was purified by column chromatography eluting with 25-50% EtOAc in hexanes to afford compound 13 (1.63 g, 57% yield, HPLC area 93% pure) as a white solid. ¹H NMR in DMSO-d6: δ 11.19 and 10.93 (two singlets with integration ratio of 1.73:1, total of 1H, same proton of two rotamers), 7.93 (d, 2H), 7.66 (d, 2H), 5.80 (s, 2H), 3.36 (s, 2H), 3.27 (s, 2H), 1.18 (s, 2H), 0.27 (q, 1H), 0.06 (s, 1H); Mass Spec: 435.0 (M+H)⁺

Step B. Synthesis of ST-246 (Route V)

Anhydrous DMF (6 mL) was added to a mixture of compound 13 (0.2 g, 0.46 mmol), methyl 2,2-difluoro-2-(fluorosulfonyl)acetate (0.44 mL, 3.45 mmol, Aldrich) and copper (I) iodide (90 mg, 0.47 mmol). The reaction mixture was stirred at ~90° C. for 4 h. LC-MS analysis at 254 nm indicated no starting material 13 remained and showed 48% HPLC area of ST-246. The reaction mixture was cooled to 45° C. and DMF was removed under reduced pressure. The residue was slurried in EtOAc (30 mL) and insoluble solid was removed by filtration. The filtrate was concentrated and purified by column chromatography eluting with 25-35% EtOAc in hexanes to afford ST-246 (55 mg, 32% yield, 95% pure by HPLC at 254 nm) as off-white solid. Analytical data (¹H NMR and LC-MS) were consistent with those of ST-246 synthesized according to WO04112718.

What is claimed is:

1. A method for producing N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide, said method comprising:

(a) reacting compound 3 of formula:

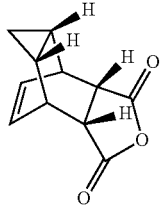

with tert-butyl carbazate (compound 5) to form compound 6 of formula:

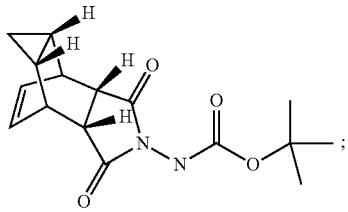

(b) reacting compound 6 with an acid to form compound 7 or salt thereof of formula:

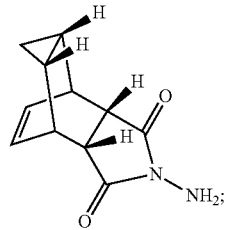

(c) reacting compound 7 with 4-(trifluoromethyl)benzoyl chloride (compound 8); and (d) collecting N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide.

2. The method of claim 1, wherein step (a) is carried under nitrogen atmosphere above room temperature.

3. The method of claim 1, wherein said acid in step (b) is HCl.

4. The method of claim 1, wherein compound 6 is dissolved in i-PrOAc prior to the reaction of step (b).

5. The method of claim 1, wherein a base is present in the reaction of step (c), wherein said base is selected from the group consisting of: pyridine, 4-dimethylaminopyridine, triethylamine and diisopropylethylamine.

6. The method of claim 1, wherein step (c) is carried out at a temperature of less than about 20° C.

7. The method of claim 1, wherein said N-[(3aR,4R,4aR,5aS,6S,6aS)-3,3a,4,4a,5,5a,6,6a-octahydro-1,3-dioxo-4,6-ethenocycloprop[f]isoindol-2(1H)-yl]-4-(trifluoromethyl)-benzamide collected in step (d) is further purified by column chromatography.

8. Compound 6 of the following formula:

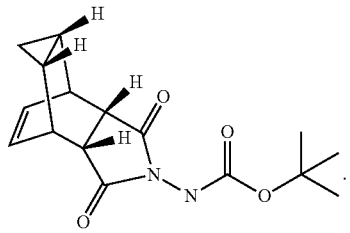

* * * * *